(12) United States Patent
Webb

(10) Patent No.: US 8,845,600 B2
(45) Date of Patent: Sep. 30, 2014

(54) SKIN CARE COMPOSITIONS AND USES THEREOF

(76) Inventor: Carly Webb, Colorado Springs, CO (US)

( * ) Notice: Subject to any disclaimer, the term of this patent is extended or adjusted under 35 U.S.C. 154(b) by 657 days.

(21) Appl. No.: 13/093,357

(22) Filed: Apr. 25, 2011

(65) Prior Publication Data

US 2012/0271251 A1    Oct. 25, 2012

(51) Int. Cl.
| | |
|---|---|
| A61M 35/00 | (2006.01) |
| A01N 65/00 | (2009.01) |
| A61K 36/00 | (2006.01) |
| A61K 31/723 | (2006.01) |
| A61Q 19/00 | (2006.01) |
| A61K 33/14 | (2006.01) |
| A61K 8/36 | (2006.01) |
| A61K 8/20 | (2006.01) |
| A61K 8/73 | (2006.01) |
| A61K 8/34 | (2006.01) |
| A61K 31/19 | (2006.01) |

(52) U.S. Cl.
CPC ............ *A61K 31/723* (2013.01); *A61K 2800/85* (2013.01); *A61Q 19/008* (2013.01); *A61Q 19/00* (2013.01); *A61K 33/14* (2013.01); *A61K 8/36* (2013.01); *A61K 8/20* (2013.01); *A61K 8/73* (2013.01); *A61K 8/34* (2013.01); *A61K 31/19* (2013.01); *A61Q 19/007* (2013.01)
USPC .......................... 604/289; 424/78.02; 424/725

(58) Field of Classification Search
USPC .......... 604/289, 290; 424/401, 484, 485, 488, 424/489, 493, 496, 499, 500
See application file for complete search history.

(56) References Cited

U.S. PATENT DOCUMENTS

| | | |
|---|---|---|
| 5,006,557 A | 4/1991 | Siu-Ming et al. |
| 5,560,915 A | 10/1996 | Koulbanis et al. |
| 5,654,013 A | 8/1997 | Taylor et al. |
| 6,083,890 A | 7/2000 | Miskiel et al. |
| 6,231,840 B1 | 5/2001 | Buck |
| 6,287,548 B1 | 9/2001 | Biener |
| 6,350,475 B1 | 2/2002 | Taylor et al. |
| 6,352,724 B1 | 3/2002 | Taylor et al. |
| 6,987,083 B2 | 1/2006 | Phillippi et al. |
| 2007/0003582 A1 | 1/2007 | Heng |
| 2007/0031363 A1 | 2/2007 | Bunker |
| 2009/0214608 A1 | 8/2009 | Monin et al. |

*Primary Examiner* — Melanie Hand
(74) *Attorney, Agent, or Firm* — Mitchell A. Rossman; Terra Nova Patent Law, PLLC

(57) ABSTRACT

Various topical compositions for skin care are disclosed. These topical composition include: one or more acidic fermentation products derived from one or more ($C_1$-$C_6$) unsubstituted straight chain alcohols and branched alcohols; one or more alkali metal halides; one or more polysaccharides; and water. Methods of treating acne, seborrheic dermatitis, effects of ageing, blemishes, cleansing and treating skin, and the like, with these various topical compositions are also provided.

4 Claims, No Drawings

SKIN CARE COMPOSITIONS AND USES THEREOF

BACKGROUND OF THE INVENTION

There are many materials available for cleansing and treating skin. These compositions include, for example, pure metallic salts of fatty acids and complex mixtures of various surfactants that are combined with medicinal agents, oils, alcohols, glycerin, vitamins, minerals, preservatives, organic materials, inorganic materials, fragrances, and coloring agents.

These known cleaning materials vary in their effectiveness, for example, in their penetration of the skin and their cleansing action, and in causing or reducing wrinkling, causing or controlling drying, and accelerating or slowing the effects of aging. Generally, the more effective materials are in cleansing the skin, the harsher they are on the skin. For example, many popular and effective skin cleaning materials cause significant drying and wrinkling, allergic reactions and other deleterious effects.

What is needed is a topical composition useful in treating acne, seborrheic dermatitis, effects of ageing, blemishes, cleansing and treating skin, and the like, but is gentle to the skin.

SUMMARY OF THE INVENTION

The present invention provides a topical composition useful in treating acne, seborrheic dermatitis, effects of ageing, blemishes, cleansing and treating skin, and the like, but is gentle to the skin. The topical composition, as described herein, softens the skin, reduces the appearance of fine lines and wrinkles, removes debris from pores, reduces the size of the skin pores, normalizes skin pH, reduces superficial skin redness, and leaves the skin hydrated.

The present invention provides a topical composition. The topical composition includes: one or more acidic fermentation products derived from one or more ($C_1$-$C_6$) unsubstituted straight chain alcohols and branched alcohols; one or more alkali metal halides; one or more polysaccharides; and water.

In one embodiment, the one or more ($C_1$-$C_6$) unsubstituted straight chain alcohols and branched alcohols each independently include methanol, ethanol, n-propanol, n-butanol, n-pentanol, n-hexanol, iso-propanol, sec-butanol, iso-butanol, tert-butanol, n-pentanol, iso-pentanol, sec-pentanol, tert-pentanol, iso-hexanol, sec-hexanol, tert-hexanol, or combinations thereof.

In one embodiment, the one or more ($C_1$-$C_6$) unsubstituted straight chain alcohols and branched alcohols include ethanol. In one embodiment, the one or more acidic fermentation products derived from one or more ($C_1$-$C_6$) unsubstituted straight chain alcohols and branched alcohols each independently include vinegar.

In one embodiment, the one or more alkali metal halides each independently include lithium fluoride, sodium fluoride, potassium fluoride, rubidium fluoride, caesium fluoride, lithium chloride, sodium chloride, potassium chloride, rubidium chloride, caesium chloride, lithium bromide, sodium bromide, potassium bromide, rubidium bromide, caesium bromide, lithium iodide, sodium iodide, potassium iodide, rubidium iodide, caesium iodide, or combinations thereof.

In one embodiment, the one or more alkali metal halides each independently include sodium chloride.

In one embodiment, the one or more polysaccharides each include starch, a gum, or a combination thereof.

In one embodiment, the gum includes xanthan gum, gum Arabic, guar gum, red gum, gum acacia, sweet gum, black gum, kauri gum, gum, tara gum, carob bean gum, carrageenan gum, alginate gum, pectin gum, konjac gum, carboxymethylcellulose gum, methylcellulose gum, hydroxyl propyl methylcellulose gum, or combinations thereof. In one embodiment, the gum is xanthan gum.

In one embodiment, the one or more acidic fermentation products derived from one or more ($C_1$-$C_6$) unsubstituted straight chain alcohols and branched alcohols are present in the topical composition from about 5 weight percent to about 50 weight percent. In one embodiment, the one or more acidic fermentation products derived from one or more ($C_1$-$C_6$) unsubstituted straight chain alcohols and branched alcohols are present in the topical composition from about 10 weight percent to about 30 weight percent. In one embodiment, the one or more acidic fermentation products derived from one or more ($C_1$-$C_6$) unsubstituted straight chain alcohols and branched alcohols are present in the topical composition from about 16 weight percent to about 22 weight percent.

In one embodiment, the one or more alkali metal halides are present in the topical composition from about 0.5 weight percent to about 30 weight percent. In one embodiment, the one or more alkali metal halides are present in the topical composition from about 1 weight percent to about 20 weight percent. In one embodiment, the one or more alkali metal halides are present in the topical composition from about 9 weight percent to about 15 weight percent.

In one embodiment, the one or more polysaccharides are present in the topical composition from about 0.5 weight percent to about 10 weight percent. In one embodiment, the one or more polysaccharides are present in the topical composition from about 1 weight percent to about 7 weight percent. In one embodiment, the one or more polysaccharides are present in the topical composition from about 3 weight percent to about 5 weight percent.

In one embodiment, the water is present in the topical composition from about 30 weight percent to about 80 weight percent. In one embodiment, the water is present in the topical composition from about 40 weight percent to about 70 weight percent. In one embodiment, the water is present in the topical composition from about 45 weight percent to about 55 weight percent.

In one embodiment, the composition further includes one or more cosmetically or pharmaceutically acceptable essential oils.

In one embodiment, the one or more cosmetically or pharmaceutically acceptable essential oils each independently include essential orange oil, essential clary sage oil, peppermint oil, clove oil, *eucalyptus* oil, lavender oil; anise essential oil, angelica essential oil, iris essential oil, fennel essential oil, cananga essential oil, caraway essential oil, cardamom essential oil, guaiacwood essential oil, cumin essential oil, Lindera essential oil, cinnamon essential oil, geranium essential oil, copaiba balsam essential oil, coriander essential oil, perilla essential oil, cedarwood essential oil, citronella essential oil, jasmine essential oil, palmarosa sofia essential oil, cedar essential oil, spearmint essential oil, Western mint essential oil, star anis essential oil, tuberose essential oil, clove essential oil, Neroli essential oil, wintergreen essential oil, tolu balsam essential oil, patchouli essential oil, rose essential oil, palmarosa essential oil, Chamaecyparis obtusa essential oil, Hiba essential oil, sandalwood essential oil, petitgrain essential oil, bay essential oil, vetivert essential oil, bergamot essential oil, Peru balsam essential oil, bois de rose essential oil, ho camphor essential oil, mandarin essential oil, *eucalyptus* essential oil, lime essential oil, lavender essential oil, linaloe essential oil, lemongrass essential oil, lemon essential oil, rosemary essential oil, Japanese mint essential oil, spice plant essential oil, or a combination thereof.

In one embodiment, the one or more cosmetically or pharmaceutically acceptable essential oils each independently include essential orange oil. In one embodiment, the one or more cosmetically or pharmaceutically acceptable essential oils each independently include essential clary sage oil.

In one embodiment, the one or more cosmetically or pharmaceutically acceptable essential oils are present in the topical composition from about 0.0001 weight percent to about 10 weight percent. In one embodiment, the one or more cosmetically or pharmaceutically acceptable essential oils are present in the topical composition from about 0.001 weight percent to about 5 weight percent. In one embodiment, the one or more cosmetically or pharmaceutically acceptable essential oils are present in the topical composition from about 0.003 weight percent to about 4 weight percent.

In one embodiment, the composition further includes one or more cosmetically or pharmaceutically acceptable non-essential oils. In one embodiment, the one or more cosmetically or pharmaceutically acceptable non-essential oils each independently include olive oil, soybean oil, safflower oil, sunflower oil, sweet almond oil, walnut oil, jojoba oil, macadamia nut oil, coconut oil, palm fruit oil, palm kernel oil, sesame oil, rapeseed oil, canola oil, rice bran oil, grape seed oil, flaxseed oil, corn oil, cocoa butter, cottonseed oil, avocado oil, apricot kernel oil, peach kernel oil, rosehip seed oil, wheat germ oil, borage seed oil, *Borago officinalis* oil, blackcurrant oil, *Calaphyllum inophyllum* oil, evening primrose oil, hazelnut oil, hemp seed oil, hyptis oil, kiwi seed oil, kukui nut oil, castor oil, *Lesquerella auriculata* oil, sea buckthorn oil, nigella sativa oil, camelina sativa oil, *Limnathes alba* oil, *Azadirachta indica* oil, plum kernel oil, *Punica granatum* oil, or a combination thereof. In one embodiment, the one or more cosmetically or pharmaceutically acceptable non-essential oils each independently include grape seed oil.

In one embodiment, the one or more cosmetically or pharmaceutically acceptable non-essential oils are present in the topical composition from about 0.1 weight percent to about 30 weight percent. In one embodiment, the one or more cosmetically or pharmaceutically acceptable non-essential oils are present in the topical composition from about 2 weight percent to about 15 weight percent. In one embodiment, the one or more cosmetically or pharmaceutically acceptable non-essential oils are present in the topical composition from about 2 weight percent to about 5 weight percent.

In one embodiment, the composition further includes one or more fruit or vegetable juices. In one embodiment, the one or more fruit or vegetable juices each independently include alfalfa, apple, apricot, banana, beet, blackberry, blueberry, cantaloupe, carrot, celery, cherry, cranberry, grape, grapefruit, green barley, lime, lemon, green lettuce, kale, kiwi, mango, orange, papaya, parsley, peach, pear, pineapple, plum, prune, raspberry, spinach, strawberry, tangerine, tomato, watermelon, wolfberry, or a combination thereof. In one embodiment, the one or more fruit or vegetable juices each independently include lime juice.

In one embodiment, the one or more fruit or vegetable juices each independently include a juice, juice concentrate, puree, extract, or combination thereof. In one embodiment, the one or more fruit or vegetable juices are present in the topical composition from about 0.1 weight percent to about 10 weight percent. In one embodiment, the one or more fruit or vegetable juices are present in the topical composition from about 1 weight percent to about 7 weight percent. In one embodiment, the one or more fruit or vegetable juices are present in the topical composition from about 3 weight percent to about 5 weight percent.

In one embodiment, the composition further includes one or more spices. In one embodiment, the one or more spices each independently include allspice, ginger root, cloves, peppercorn, garlic, tarragon, dill, marjoram, sage, basil, thyme, oregano, cumin, cilantro, chili powder, coriander, mustard, mustard seed, rosemary, paprika, curry, cardamon, fennel seeds, bay, laurel, cloves, fenugreek, parsley, turmeric, chives, scallions, leeks, shallots, cayenne pepper, bell pepper, hot peppers, nutmeg, brown sugar, or a combination thereof. In one embodiment, the one or more spices each independently include allspice, ginger root, cloves, and peppercorn.

In one embodiment, the one or more spices are present in the topical composition from about 0.01 weight percent to about 10 weight percent. In one embodiment, the one or more spices are present in the topical composition from about 0.1 weight percent to about 5 weight percent. In one embodiment, the one or more spices are present in the topical composition from about 0.2 weight percent to about 3 weight percent.

In one embodiment, the composition further includes one or more animal or plant extracts. In one embodiment, the one or more animal or plant extracts each independently include mint extract, *hibiscus* extract, elderberry extract, Siberian ginseng extract, Phellodendron bark extract, *Coffea Arabica* extract, White birch extract, *Mentha piperita* extract, *Thymus* extract, Tea extract, *Hamamelis* extract, *Isodonis japonica* extract, Coltsfoot extract, *Vitis vinifera* leaf extract, *Humulus lupulus* extract, Horse chestnut extract, *Melissa officinalis* extract, Acerola extract, Rose fruit extract, *Actinidia chinensis* fruit extract, Arnica extract, *Scutellaria baicalensis* root extract, *Coptis rhizome* extract, *Lamium album* extract, Cattail extract, *Chamomilla recutita* extract, *Artemisia capillaris* flower extract, *Glycyrrhiza glabra* extract, *Gardenia florida* extract, *Sasa veitchii* extract, *Gentiana* extract, *Clammellia sinensis* extract, *Symphytum officinale* leaf extract, *Perilla ocymoides* leaf extract, *Lithospermum erythrorhizone* root extract, Linden extract, *Spiraea ulmaria* extract, *Paeonia albiflora* root extract, *Lonicera japonica* extract, *Salvia officinalis* extract, *Hedera helix* extract, *Sambucus nigra* flower extract, *Achillea millefolium* extract, *Swertia japonica* extract, Mulberry root extract, *Calendula officinalis* flower extract, *Eriobotrya japonica* leaf extract, *Prunus persica* leaf extract, *Centaurea cyanus* flower extract, *Saxifrage sarmentosa* extract, Mugwort extract, *Lactuca scariola* sativa extract, *Anthemis nobilis* flower extract, and *Sanguisorba officinalis* root extract, or a combination thereof. In one embodiment, the one or more animal or plant extracts each independently include mint extract, *hibiscus* extract, elderberry extract.

In one embodiment, the one or more animal or plant extracts are present in the topical composition from about 0.1 weight percent to about 50 weight percent. In one embodiment, the one or more animal or plant extracts are present in the topical composition from about 1 weight percent to about 25 weight percent. In one embodiment, the one or more animal or plant extracts are present in the topical composition from about 2 weight percent to about 5 weight percent.

In one embodiment, the composition further includes one or more anti-acne agents, one or more anti-itch agents, one or more anti-oxidants, one or more anti-microbial agents, one or more anti-fungal agents, one or more non-steroid cosmetic soothing agents, one or more skin conditioning agents, one or more anti-foaming agents, one or more buffers, one or more neutralizing agents, one or more pH adjusting agents, one or more coloring agents, one or more decoloring agents, one or more emollients, one or more emulsifying agents, one or more emulsion stabilizers, one or more viscosity builders, one or more humectants, one or more odorants, one or more preservatives, one or more antioxidants, one or more chemical stabilizers, one or more thickening agents, one or more steroids, one or more organic solvents, or combinations thereof. In one embodiment, the topical composition includes a solution, spray, lotion, gel, cream, or ointment.

In one embodiment, the composition further includes one or more precious metals, one or more semi-precious metals, or a combination thereof. In one embodiment, the one or more precious metals each independently include gold, silver, copper, platinum, palladium ruthenium, rhodium, osmium, iridium, germanium, gallium, or a combination thereof. In one embodiment, the one or more semi-precious metals each independently include nickel, bismuth, tellurium, zinc, iron, or a combination thereof.

The present invention provides a topical composition. The topical composition includes: one or more ($C_1$-$C_6$) unsubstituted straight chain and branched carboxylic acids; one or more alkali metal halides; one or more polysaccharides; and water.

In one embodiment, the one or more ($C_1$-$C_6$) unsubstituted straight chain and branched carboxylic acids each independently include formic acid, acetic acid, n-propanoic acid, n-butanoic acid, n-pentanoic acid, n-hexanoic acid, iso-propanoic acid, sec-butanoic acid, iso-butanoic acid, tert-butanoic acid, n-pentanoic acid, iso-pentanoic acid, sec-pentanoic acid, tert-pentanoic acid, iso-hexanoic acid, sec-hexanoic acid, tert-hexanoic acid, or combinations thereof.

In one embodiment, the one or more ($C_1$-$C_6$) unsubstituted straight chain and branched carboxylic acids each independently include acetic acid.

The present invention provides a topical composition. The topical composition includes: vinegar; one or more alkali metal halides; one or more polysaccharides; and water.

The present invention provides a topical composition. The topical composition includes: vinegar; one or more alkali metal halides; xanthan gum; and water.

The present invention provides a topical composition. The topical composition includes: vinegar; sodium chloride; xanthan gum; and water.

The present invention provides a topical composition. The topical composition includes: about 5 weight percent to about 50 weight percent vinegar; about 0.5 weight percent to about 30 weight percent sodium chloride; about 0.5 weight percent to about 10 weight percent xanthan gum; and about 30 weight percent to about 80 weight percent water.

The present invention provides a topical composition. The topical composition includes: about 10 weight percent to about 30 weight percent vinegar; about 1 weight percent to about 20 weight percent sodium chloride; about 1 weight percent to about 5 weight percent xanthan gum; and about 40 weight percent to about 70 weight percent water.

The present invention provides a topical composition. The topical composition includes: about 13 weight percent to about 22 weight percent vinegar; about 2 weight percent to about 12 weight percent sodium chloride; about 2 weight percent to about 4 weight percent xanthan gum; and about 50 weight percent to about 60 weight percent water.

The present invention provides a topical composition. The topical composition consists of: about 5 weight percent to about 50 weight percent vinegar; about 0.5 weight percent to about 30 weight percent sodium chloride; about 0.5 weight percent to about 10 weight percent xanthan gum; and about 30 weight percent to about 80 weight percent water.

The present invention provides a topical composition. The topical composition consists of: about 10 weight percent to about 30 weight percent vinegar; about 1 weight percent to about 20 weight percent sodium chloride; about 1 weight percent to about 5 weight percent xanthan gum; and about 40 weight percent to about 70 weight percent water.

The present invention provides a topical composition. The topical composition consists of: about 13 weight percent to about 22 weight percent vinegar; about 2 weight percent to about 12 weight percent sodium chloride; about 2 weight percent to about 4 weight percent xanthan gum; and about 50 weight percent to about 60 weight percent water.

The present invention provides a topical composition. The topical composition consists of: about 5 weight percent to about 50 weight percent vinegar; about 0.5 weight percent to about 30 weight percent sodium chloride; about 0.5 weight percent to about 10 weight percent xanthan gum; and about 30 weight percent to about 80 weight percent water.

The present invention provides a topical composition. The topical composition consists of: about 10 weight percent to about 30 weight percent vinegar; about 1 weight percent to about 20 weight percent sodium chloride; about 1 weight percent to about 5 weight percent xanthan gum; and about 40 weight percent to about 70 weight percent water.

The present invention provides a topical composition. The topical composition consists of: about 13 weight percent to about 22 weight percent vinegar; about 2 weight percent to about 12 weight percent sodium chloride; about 2 weight percent to about 4 weight percent xanthan gum; and about 50 weight percent to about 60 weight percent water.

The present invention provides a topical composition. The topical composition includes: about 21.1 weight percent vinegar; about 14.2 weight percent sodium chloride; about 2.8 weight percent xanthan gum; and about 52.0 weight percent water.

The present invention provides a topical composition. The topical composition consists essentially of: about 21.1 weight percent vinegar; about 14.2 weight percent sodium chloride; about 2.8 weight percent xanthan gum; and about 52.0 weight percent water.

The present invention provides a topical composition. The topical composition consists of: about 21.1 weight percent vinegar; about 14.2 weight percent sodium chloride; about 2.8 weight percent xanthan gum; and about 52.0 weight percent water.

The present invention provides a topical composition. The topical composition includes: about 19.9 weight percent vinegar; about 11.1 weight percent sodium chloride; about 2.6 weight percent xanthan gum; and about 54.4 weight percent water.

The present invention provides a topical composition. The topical composition consists essentially of: about 19.9 weight percent vinegar; about 11.1 weight percent sodium chloride; about 2.6 weight percent xanthan gum; and about 54.4 weight percent water.

The present invention provides a topical composition. The topical composition consists of: about 19.9 weight percent vinegar; about 11.1 weight percent sodium chloride; about 2.6 weight percent xanthan gum; and about 54.4 weight percent water.

The present invention provides a topical composition. The topical composition includes: about 16.3 weight percent vinegar; about 9.6 weight percent sodium chloride; about 2.1 weight percent xanthan gum; and about 53.7 weight percent water.

The present invention provides a topical composition. The topical composition consists essentially of: about 16.3 weight percent vinegar; about 9.6 weight percent sodium chloride; about 2.1 weight percent xanthan gum; and about 53.7 weight percent water.

The present invention provides a topical composition. The topical composition consists of: about 16.3 weight percent vinegar; about 9.6 weight percent sodium chloride; about 2.1 weight percent xanthan gum; and about 53.7 weight percent water.

The present invention provides a topical composition. The topical composition includes: about 21.1 weight percent vinegar; about 14.2 weight percent sodium chloride; about 2.8 weight percent xanthan gum; about 52.0 weight percent water; about 3.4 weight percent *hibiscus* extract; about 0.6 weight percent tea leaves; about 0.003 weight percent essential spearmint oil; about 0.2 weight percent essential orange oil; about 0.3 weight percent ground nutmeg; and about 5.26 weight percent brown sugar.

The present invention provides a topical composition. The topical composition consists essentially of: about 21.1 weight percent vinegar; about 14.2 weight percent sodium chloride; about 2.8 weight percent xanthan gum; about 52.0 weight percent water; about 3.4 weight percent *hibiscus* extract; about 0.6 weight percent tea leaves; about 0.003 weight percent essential spearmint oil; about 0.2 weight percent essential orange oil; about 0.3 weight percent ground nutmeg; and about 5.26 weight percent brown sugar.

The present invention provides a topical composition. The topical composition consists of: about 21.1 weight percent vinegar; about 14.2 weight percent sodium chloride; about 2.8 weight percent xanthan gum; about 52.0 weight percent water; about 3.4 weight percent *hibiscus extract;* about 0.6 weight percent tea leaves; about 0.003 weight percent essential spearmint oil; about 0.2 weight percent essential orange oil; about 0.3 weight percent ground nutmeg; and about 5.26 weight percent brown sugar.

The present invention provides a topical composition. The topical composition includes: about 16.3 weight percent vinegar; about 9.6 weight percent sodium chloride; about 2.1 weight percent xanthan gum; about 53.7 weight percent water; about 6.5 weight percent elderberry extract; about 9.1 weight percent grape seed oil; about 0.7 weight percent allspice; about 0.4 weight percent tea leaves; about 1.2 weight percent ground dried sea kelp; about 0.08 weight percent essential orange oil; and about 1.8 weight percent *eucalyptus* essential oil.

The present invention provides a topical composition. The topical composition consists essentially of: about 16.3 weight percent vinegar; about 9.6 weight percent sodium chloride; about 2.1 weight percent xanthan gum; about 53.7 weight percent water; about 6.5 weight percent elderberry extract; about 9.1 weight percent grape seed oil; about 0.7 weight percent allspice; about 0.4 weight percent tea leaves; about 1.2 weight percent ground dried sea kelp; about 0.08 weight percent essential orange oil; and about 1.8 weight percent *eucalyptus* essential oil.

The present invention provides a topical composition. The topical composition consists of: about 16.3 weight percent vinegar; about 9.6 weight percent sodium chloride; about 2.1 weight percent xanthan gum; about 53.7 weight percent water; about 6.5 weight percent elderberry extract; about 9.1 weight percent grape seed oil; about 0.7 weight percent allspice; about 0.4 weight percent tea leaves; about 1.2 weight percent ground dried sea kelp; about 0.08 weight percent essential orange oil; and about 1.8 weight percent *eucalyptus* essential oil.

The present invention provides a topical composition. The topical composition includes: about 19.9 weight percent vinegar; about 11.1 weight percent sodium chloride; about 2.6 weight percent xanthan gum; about 49.3 weight percent water; about 3.7 weight percent grape seed oil; about 4.1 weight percent lime juice; about 0.4 weight percent cloves; about 0.2 weight percent peppercorn; about 8.0 weight percent mint extract; about 0.4 weight percent orange essential orange oil; and about 0.1 weight percent essential rosemary oil.

The present invention provides a topical composition. The topical composition consists essentially of: about 19.9 weight percent vinegar; about 11.1 weight percent sodium chloride; about 2.6 weight percent xanthan gum; about 49.3 weight percent water; about 3.7 weight percent grape seed oil; about 4.1 weight percent lime juice; about 0.4 weight percent cloves; about 0.2 weight percent peppercorn; about 8.0 weight percent mint extract; about 0.4 weight percent orange essential orange oil; and about 0.1 weight percent essential rosemary oil.

The present invention provides a topical composition. The topical composition consists of: about 19.9 weight percent vinegar; about 11.1 weight percent sodium chloride; about 2.6 weight percent xanthan gum; about 49.3 weight percent water; about 3.7 weight percent grape seed oil; about 4.1 weight percent lime juice; about 0.4 weight percent cloves; about 0.2 weight percent peppercorn; about 8.0 weight percent mint extract; about 0.4 weight percent orange essential orange oil; and about 0.1 weight percent essential rosemary oil.

The present invention provides a method of treating acne. The method includes: applying a composition to the skin of a human including: one or more acidic fermentation products derived from one or more ($C_1$-$C_6$) unsubstituted straight chain alcohols and branched alcohols; one or more alkali metal halides; one or more polysaccharides; and water.

The present invention provides a method of treating acne. The method includes: applying a composition to the skin of a human including: vinegar; one or more alkali metal halides; one or more polysaccharides; and water.

The present invention provides a method of treating acne. The method includes: applying a composition to the skin of a human including: vinegar; one or more alkali metal halides; xanthan gum; and water.

The present invention provides a method of treating acne. The method includes: applying a composition to the skin of a human including: vinegar; sodium chloride; xanthan gum; and water.

The present invention provides a method of treating seborrheic dermatitis. The method includes: applying a composition to the skin of a human including: one or more acidic fermentation products derived from one or more ($C_1$-$C_6$) unsubstituted straight chain alcohols and branched alcohols; one or more alkali metal halides; one or more polysaccharides; and water.

The present invention provides a method of treating seborrheic dermatitis. The method includes: applying a composition to the skin of a human including: vinegar; one or more alkali metal halides; one or more polysaccharides; and water.

The present invention provides a method of treating seborrheic dermatitis. The method includes: applying a composition to the skin of a human including: vinegar; one or more alkali metal halides; xanthan gum; and water.

The present invention provides a method of treating seborrheic dermatitis. The method includes: applying a composition to the skin of a human including: vinegar; sodium chloride; xanthan gum; and water.

The present invention provides a method of treating the effects of ageing. The method includes: applying a composition to the skin of a human including: one or more acidic fermentation products derived from one or more ($C_1$-$C_6$) unsubstituted straight chain alcohols and branched alcohols; one or more alkali metal halides; one or more polysaccharides; and water.

The present invention provides a method of treating the effects of ageing. The method includes: applying a composition to the skin of a human including: vinegar; one or more alkali metal halides; one or more polysaccharides; and water.

The present invention provides a method of treating the effects of ageing. The method includes: applying a composition to the skin of a human including: vinegar; one or more alkali metal halides; xanthan gum; and water.

The present invention provides a method of treating the effects of ageing. The method includes: applying a composition to the skin of a human including: vinegar; sodium chloride; xanthan gum; and water.

The present invention provides a method of treating blemishes associated with diseases. The method includes: applying a composition to the skin of a human including: one or more acidic fermentation products derived from one or more ($C_1$-$C_6$) unsubstituted straight chain alcohols and branched alcohols; one or more alkali metal halides; one or more polysaccharides; and water.

The present invention provides a method of treating blemishes associated with diseases. The method includes: applying a composition to the skin of a human including: vinegar; one or more alkali metal halides; one or more polysaccharides; and water.

The present invention provides a method of treating blemishes associated with diseases. The method includes: applying a composition to the skin of a human including: vinegar; one or more alkali metal halides; xanthan gum; and water.

The present invention provides a method of treating blemishes associated with diseases. The method includes: applying a composition to the skin of a human including: vinegar; sodium chloride; xanthan gum; and water.

The present invention provides method of cleansing and treating skin. The method includes: applying a composition to the skin of a human including: one or more acidic fermentation products derived from one or more ($C_1$-$C_6$) unsubstituted straight chain alcohols and branched alcohols; one or more alkali metal halides; one or more polysaccharides; and water, allowing the composition to be at least partially absorbed by the skin; and washing the treated skin.

The present invention provides method of cleansing and treating skin. The method includes: applying a composition to the skin of a human including: vinegar; one or more alkali metal halides; one or more polysaccharides; and water; allowing the composition to be at least partially absorbed by the skin; and washing the treated skin.

The present invention provides method of cleansing and treating skin. The method includes: applying a composition to the skin of a human including: vinegar; one or more alkali metal halides; xanthan gum; and water; allowing the composition to be at least partially absorbed by the skin; and washing the treated skin.

The present invention provides method of cleansing and treating skin. The method includes: applying a composition to the skin of a human including: vinegar; sodium chloride; xanthan gum; and water; allowing the composition to be at least partially absorbed by the skin; and washing the treated skin.

The present invention provides a therapeutic kit. The kit includes: a topical composition including: one or more acidic fermentation products derived from one or more ($C_1$-$C_6$) unsubstituted straight chain alcohols and branched alcohols; one or more alkali metal halides; one or more polysaccharides; and water; and instructions for the use of the topical composition and dosage regime thereto.

The present invention provides a therapeutic kit. The kit includes: a topical composition including: vinegar; one or more alkali metal halides; one or more polysaccharides; and water; and instructions for the use of the topical composition and dosage regime thereto.

The present invention provides a therapeutic kit. The kit includes: a topical composition including: vinegar; one or more alkali metal halides; xanthan gum; and water; and instructions for the use of the topical composition and dosage regime thereto.

The present invention provides a therapeutic kit. The kit includes: a topical composition including: vinegar; sodium chloride; xanthan gum; and water; and instructions for the use of the topical composition and dosage regime thereto.

DETAILED DESCRIPTION OF THE INVENTION

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993, *The American Heritage Dictionary of the English Language*, Houghton Mifflin, Boston Mass., 1981, and *Hawley's Condensed Chemical Dictionary*, $14^{th}$ edition, Wiley Europe, 2002.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "agent" refers to anything that may have an impact on any living system such as a cell, nerve or tissue. For examples, the agent can be a chemical agent. The agent can also be a biological agent. The agent may comprise at least one known component. The agent can also be a physical agent.

As used herein, the phrase "animal extract" refers to any substance extracted from an animal.

As used herein, the phrase "anti-aging" refers to preventing and improving skin wrinkles, sagging or hardening and the like as well as maintaining skin in a resilient, youthful, elastic, and healthy state.

As used herein, the phrase "anti-wrinkle effects" refer to any arbitrary effects that prevent wrinkle formation or improve wrinkles that have already been formed.

As used herein, the term "dermis" refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

As used herein, the term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the term "epidermis" refers to the outer, protective, nonvascular layer of the skin of vertebrates, covering the dermis. The epidermis consists histologically of five layers, i.e. the stratum corneum, the stratum lucidum, the stratum granulosum, the stratum spinosum, and the stratum basale.

As used herein, the terms "include," "for example," "such as," and the like are used illustratively and are not intended to limit the present invention.

As used herein, the term "liquid" refers to a substance that undergoes continuous deformation under a shearing stress. See, e.g., *Concise Chemical and Technical Dictionary*, $4^{th}$ Edition, Chemical Publishing Co., Inc., p. 707, New York, N.Y. (1986).

As used herein, the term "patient" refers to a warm-blooded animal, and preferably a mammal, for example, a human.

As used herein, the terms "optional" or "optionally" mean that the subsequently described event or condition may but need not occur, and that the description includes instances where the event or condition occurs and instances in which it does not.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacoepia* describe the analytical criteria to assess the pharmaceutical acceptability of numerous ingredients of interest.

As used herein, the phrase "plant extract" refers to any substance extracted from a plant.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "skin" refers to the external tissue layer in humans and animals consisting of epidermis and dermis.

As used herein, the phrase "subcutaneous tissue layer" refers to a tissue layer located below the skin. This tissue layer is typically characterized by a loose meshwork of connective tissue such as collagen and elastic fibers.

As used herein, the terms "therapy," and "therapeutic" refer to either "treatment" or "prevention," thus, agents that either treat damage or prevent damage are "therapeutic."

As used herein, the term "tissue" refers to an organized biomaterial usually composed of cells.

As used herein, the phrase "therapeutic kit" refers to a collection of components that can be used in a medical treatment.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells which line hollow organs or body cavities).

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the term "treatment," covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and one or more (C) relieving the disease, i.e., causing regression of the disease.

As used herein, the term "vinegar" refers to a sour-tasting liquid containing acetic acid, obtained by fermenting dilute alcoholic liquids.

The present invention provides a topical composition useful in treating acne, seborrheic dermatitis, effects of ageing, blemishes, cleansing and treating skin, and the like, but is gentle to the skin. The topical composition, as described herein, softens the skin, reduces the appearance of fine lines and wrinkles, removes debris from pores, reduces the size of the skin pores, normalizes skin pH, reduces superficial skin redness, and leaves the skin hydrated.

The present invention provides a topical composition. The topical composition includes: one or more acidic fermentation products derived from one or more ($C_1$-$C_6$) unsubstituted straight chain alcohols and branched alcohols; one or more alkali metal halides; one or more polysaccharides; and water.

Suitable one or more ($C_1$-$C_6$) unsubstituted straight chain alcohols and branched alcohols include, for example, methanol, ethanol, n-propanol, n-butanol, n-pentanol, n-hexanol, iso-propanol, sec-butanol, iso-butanol, tert-butanol, n-pentanol, iso-pentanol, sec-pentanol, tert-pentanol, iso-hexanol, sec-hexanol, tert-hexanol, or combinations thereof.

Preferably, the one or more ($C_1$-$C_6$) unsubstituted straight chain alcohols and branched alcohols include, for example, ethanol. Preferably, the one or more acidic fermentation products derived from one or more ($C_1$-$C_6$) unsubstituted straight chain alcohols and branched alcohols include, for example, vinegar.

Suitable vinegars include, for example, rice vinegars, grain vinegars, fruit vinegars, brewed vinegars, synthetic vinegars, and the like, or combinations thereof. Suitable rice vinegars include, for example, rice vinegars, brown rice vinegars, and the like, or combinations thereof. Suitable grain vinegar include, for example, sake-lees vinegars, malt vinegars, and the like, or combinations thereof. Suitable fruit vinegars include, for example, apple vinegars, wine vinegars, pineapple vinegars, and the like, or combinations thereof.

Suitable alkali metal halides include, for example, lithium fluoride, sodium fluoride, potassium fluoride, rubidium fluoride, caesium fluoride, lithium chloride, sodium chloride, potassium chloride, rubidium chloride, caesium chloride, lithium bromide, sodium bromide, potassium bromide, rubidium bromide, caesium bromide, lithium iodide, sodium iodide, potassium iodide, rubidium iodide, caesium iodide, or combinations thereof. Preferably, the one or more alkali metal halides include, for example, sodium chloride.

Suitable polysaccharides include, for example, starch, a gum, or a combination thereof.

Preferably, the gums include, for example, xanthan gum, gum Arabic, guar gum, red gum, gum acacia, sweet gum, black gum, kauri gum, gum, tara gum, carob bean gum, carrageenan gum, alginate gum, pectin gum, konjac gum, carboxymethylcellulose gum, methylcellulose gum, hydroxyl propyl methylcellulose gum, or combinations thereof, and more preferably, the gum is xanthan gum.

Preferably, the one or more acidic fermentation products derived from one or more ($C_1$-$C_6$) unsubstituted straight chain alcohols and branched alcohols are present in the topical composition from about 5 weight percent to about 50 weight percent, more preferably, from about 10 weight percent to about 30 weight percent, and most preferably, from about 16 weight percent to about 22 weight percent.

Preferably, the one or more alkali metal halides are present in the topical composition from about 0.5 weight percent to about 30 weight percent, more preferably, from about 1 weight percent to about 20 weight percent, and most preferably, from about 9 weight percent to about 15 weight percent.

Preferably, the one or more polysaccharides are present in the topical composition from about 0.5 weight percent to about 10 weight percent, more preferably, from about 1 weight percent to about 7 weight percent, and most preferably, from about 3 weight percent to about 5 weight percent.

Preferably, the water is present in the topical composition from about 30 weight percent to about 80 weight percent, more preferably, from about 40 weight percent to about 70 weight percent, and most preferably, from about 45 weight percent to about 55 weight percent.

In one embodiment, the composition further includes, for example, one or more cosmetically or pharmaceutically acceptable essential oils.

Suitable cosmetically or pharmaceutically acceptable essential oils include, for example, essential orange oil, essential clary sage oil, peppermint oil, clove oil, *eucalyptus* oil, lavender oil; anise essential oil, angelica essential oil, iris essential oil, fennel essential oil, cananga essential oil, caraway essential oil, cardamom essential oil, guaiacwood essential oil, cumin essential oil, Lindera essential oil, cinnamon essential oil, geranium essential oil, copaiba balsam essential oil, coriander essential oil, perilla essential oil, cedarwood essential oil, citronella essential oil, jasmine essential oil, palmarosa sofia essential oil, cedar essential oil, spearmint essential oil, Western mint essential oil, star anis essential oil, tuberose essential oil, clove essential oil, Neroli essential oil, wintergreen essential oil, tolu balsam essential oil, patchouli essential oil, rose essential oil, palmarosa essential oil, *Chamaecyparis obtusa* essential oil, Hiba essential oil, sandalwood essential oil, petitgrain essential oil, bay essential oil, vetivert essential oil, bergamot essential oil, Peru balsam essential oil, bois de rose essential oil, ho camphor essential oil, mandarin essential oil, *eucalyptus* essential oil, lime essential oil, lavender essential oil, linaloe essential oil, lemongrass essential oil, lemon essential oil, rosemary essential oil, Japanese mint essential oil, spice plant essential oil, or a combination thereof.

Preferably, the one or more cosmetically or pharmaceutically acceptable essential oils include, for example, essential orange oil. Preferably, the one or more cosmetically or pharmaceutically acceptable essential oils include, for example, essential clary sage oil.

Preferably, the one or more cosmetically or pharmaceutically acceptable essential oils are present in the topical composition from about 0.0001 weight percent to about 10 weight percent, more preferably, from about 0.001 weight percent to about 5 weight percent, and most preferably, from about 0.003 weight percent to about 4 weight percent.

In one embodiment, the composition further includes, for example, one or more cosmetically or pharmaceutically acceptable non-essential oils. Suitable cosmetically or pharmaceutically acceptable non-essential oils include, for example, olive oil, soybean oil, safflower oil, sunflower oil, sweet almond oil, walnut oil, jojoba oil, macadamia nut oil, coconut oil, palm fruit oil, palm kernel oil, sesame oil, rapeseed oil, canola oil, rice bran oil, grape seed oil, flaxseed oil, corn oil, cocoa butter, cottonseed oil, avocado oil, apricot kernel oil, peach kernel oil, rosehip seed oil, wheat germ oil, borage seed oil, *Borago officinalis* oil, blackcurrant oil, *Calaphyllum inophyllum* oil, evening primrose oil, hazelnut oil, hemp seed oil, hyptis oil, kiwi seed oil, kukui nut oil, castor oil, *Lesquerella auriculata* oil, sea buckthorn oil, nigella sativa oil, camelina sativa oil, *Limnathes alba* oil, *Azadirachta indica* oil, plum kernel oil, *Punica granatum* oil, or a combination thereof. Preferably, the one or more cosmetically or pharmaceutically acceptable non-essential oils include, for example, grape seed oil.

Preferably, the one or more cosmetically or pharmaceutically acceptable non-essential oils are present in the topical composition from about 0.1 weight percent to about 30 weight percent, more preferably, from about 2 weight percent to about 15 weight percent, and most preferably, from about 2 weight percent to about 5 weight percent.

In one embodiment, the composition further includes, for example, one or more fruit or vegetable juices. Suitable fruit or vegetable juices include, for example, alfalfa, apple, apricot, banana, beet, blackberry, blueberry, cantaloupe, carrot, celery, cherry, cranberry, grape, grapefruit, green barley, lime, lemon, green lettuce, kale, kiwi, mango, orange, papaya, parsley, peach, pear, pineapple, plum, prune, raspberry, spinach, strawberry, tangerine, tomato, watermelon, wolfberry, or a combination thereof. Preferably, the one or more fruit or vegetable juices include, for example, lime juice.

Suitable fruit or vegetable juices include, for example, a juice, juice concentrate, puree, extract, or combination thereof.

Preferably, the one or more fruit or vegetable juices are present in the topical composition from about 0.1 weight percent to about 10 weight percent, more preferably, from about 1 weight percent to about 7 weight percent, and most preferably, from about 3 weight percent to about 5 weight percent.

In one embodiment, the composition further includes, for example, one or more spices. Suitable spices include, for example, allspice, ginger root, cloves, peppercorn, garlic, tarragon, dill, marjoram, sage, basil, thyme, oregano, cumin, cilantro, chili powder, coriander, mustard, mustard seed, rosemary, paprika, curry, cardamon, fennel seeds, bay, laurel, cloves, fenugreek, parsley, turmeric, chives, scallions, leeks, shallots, cayenne pepper, bell pepper, hot peppers, nutmeg, brown sugar, or a combination thereof. Preferably, the one or more spices include, for example, allspice, ginger root, cloves, and peppercorn.

Preferably, the one or more spices are present in the topical composition from about 0.01 weight percent to about 10 weight percent, more preferably, from about 0.1 weight percent to about 5 weight percent, and most preferably, from about 0.2 weight percent to about 3 weight percent.

In one embodiment, the composition further includes, for example, one or more animal or plant extracts. Suitable animal or plant extracts include, for example, mint extract, *hibiscus* extract, elderberry extract, Siberian ginseng extract, *Phellodendron* bark extract, *Coffea Arabica* extract, White birch extract, *Mentha piperita* extract, *Thymus* extract, Tea extract, *Hamamelis* extract, *Isodonis japonica* extract, Coltsfoot extract, *Vitis vinifera* leaf extract, *Humulus lupulus* extract, Horse chestnut extract, *Melissa officinalis* extract, Acerola extract, Rose fruit extract, *Actinidia chinensis* fruit extract, Arnica extract, *Scutellaria baicalensis* root extract, *Coptis rhizome* extract, *Lamium* album extract, Cattail extract, *Chamomilla recutita* extract, *Artemisia capillaris* flower extract, *Glycyrrhiza glabra* extract, *Gardenia florida* extract, *Sasa veitchii* extract, *Gentiana* extract, *Clammellia sinensis* extract, *Symphytum officinale* leaf extract, *Perilla ocymoides* leaf extract, *Lithospermum erythrorhizone* root extract, Linden extract, *Spiraea ulmaria* extract, *Paeonia albiflora* root extract, *Lonicera japonica* extract, *Salvia officinalis* extract, *Hedera helix* extract, *Sambucus nigra* flower extract, *Achillea millefolium* extract, *Swertia japonica* extract, Mulberry root extract, *Calendula officinalis* flower extract, *Eriobotrya japonica* leaf extract, *Prunus persica* leaf extract, *Centaurea cyanus* flower extract, *Saxifrage sarmentosa* extract, Mugwort extract, *Lactuca scariola sativa* extract, *Anthemis nobilis* flower extract, and *Sanguisorba officinalis* root extract, or a combination thereof. Preferably, the one or more animal or plant extracts include, for example, mint extract, *hibiscus* extract, elderberry extract.

Preferably, the one or more animal or plant extracts are present in the topical composition from about 0.1 weight percent to about 50 weight percent, more preferably, from about 1 weight percent to about 25 weight percent, and most preferably, from about 2 weight percent to about 5 weight percent.

In one embodiment, the composition further includes, for example, one or more anti-acne agents, one or more anti-itch agents, one or more anti-oxidants, one or more anti-microbial agents, one or more anti-fungal agents, one or more non-steroid cosmetic soothing agents, one or more skin conditioning agents, one or more anti-foaming agents, one or more buffers, one or more neutralizing agents, one or more pH adjusting agents, one or more coloring agents, one or more decoloring agents, one or more emollients, one or more emulsifying agents, one or more emulsion stabilizers, one or more viscosity builders, one or more humectants, one or more odorants, one or more preservatives, one or more antioxidants, one or more chemical stabilizers, one or more thickening agents, one or more steroids, one or more organic solvents, or combinations thereof.

In one embodiment, the topical composition includes, for example, a solution, spray, lotion, gel, cream, or ointment.

In one embodiment, the composition further includes, for example, one or more precious metals, one or more semi-precious metals, or a combination thereof. Preferably, the one or more precious metals include, for example, gold, silver, copper, platinum, palladium ruthenium, rhodium, osmium, iridium, germanium, gallium, or a combination thereof. Preferably, the one or more semi-precious metals include, for example, nickel, bismuth, tellurium, zinc, iron, or a combination thereof.

The topical composition may be used in many forms, preferably, a solution, spray, lotion, gel, cream, or ointment, and more preferably as a lotion.

The topical composition may also include, for example, one or more solvents, one or more thickening agents, one or more penetration enhancers, one or more wetting agents, one or more lubricants, one or more emollients, one or more fragrances, one or more pigments, or a combination thereof.

Various methods of making the topical composition are also provided.

Various kits are also provided. Typically, the kits include a topical composition and instructions for the use of the topical composition and dosage regime thereto.

The topical compositions, as described herein, may also include one or more optional ingredients, for example, palliative agents, skin conditioning agents, emollients, humectants, odorants, preservatives, solvents, thickening, stiffening and suspending agents, other agents, or a combination thereof.

Typically, the one or more optional ingredients, if present, are present in an amount of about 0.001% to about 30%, about 3% to about 25%, or about 5% to about 15%, by weight. Illustratively, one or more emollients are present in a total amount of about 0.001%, about 0.25%, about 0.5%, about 0.75%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight percent.

Suitable palliative agents include, for example, menthol, camphor, phenol, allantoin, benzocaine, corticosteroids, phenol, zinc oxide, camphor, pramoxine, dimethicone, meradimate, octinoxate, octisalate, oxybenzone, dyclonine, benzyl alcohol, mineral oil, propylene glycol, titanium dioxide, magnesium stearate, and the like, or a combination thereof.

Suitable skin conditioning agents include, for example, mineral oil, petrolatum, dimethicone, dimethicone copolyol, cationic monomers and polymers (such as guar hydroxypropyl trimonium chloride and distearyl dimethyl ammonium chloride), and combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose, and combinations thereof.

Suitable emollients include, for example, caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea, and combinations thereof.

Suitable humectants include, for example, glycerin, propylene glycol, sorbitol, urea, and combinations thereof.

Suitable odorants include, for example, hypoallergenic perfume, menthol, and combinations thereof.

Suitable preservatives, antioxidants, and chemical stabilizers include, for example, alcohol, benzyl alcohol, butylated hydroxyanisole, butylparaben, calcium acetate, castor oil, chlorocresol, 4-chloro-m-cresol, citric acid, disodium edetate, edetate disodium, ethoxylated alcohol, ethyl alcohol, glycerin, methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, zinc stearate, and combinations thereof.

Suitable solvents include, for example, alcohol, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, and SD alcohol 40, triglycerides of saturated fatty acids, and combinations thereof.

Suitable thickening, stiffening and suspending agents include, for example, aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, bentonite, and combinations thereof.

Other optional agents may be added to the composition including, for example, aloe, arachis oil, benzoic acid, cocoa butter, coenzyme Q10, Q10, dimethicone, *eucalyptus* oil, resorcinol, retinol, retinyl palmitate, retinyl acetate, fennel extract, whey protein, ceramide, silicone, alpha-hydroxy acids, beta-hydroxy acids, sorbitol, vitamin A, vitamin B, vitamin C, vitamin D, vitamin E, and vitamin K. Unless otherwise indicated, the composition will generally contain less than about 5% by weight and typically less than about 1% by weight of the above-ingredients.

The topical compositions, as described herein, may be applied in a single administration or in multiple administrations. The compositions are topically applied for at least one day, at least two days, at least three days, at least four days, at least 5 days, once a week, at least twice a week, at least once a day, at least twice a day, multiple times daily, multiple times weekly, biweekly, at least once a month, or any combination thereof.

The topical compositions, as described herein, may be topically applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years.

Preferably, the composition is applied topically to the area of pain until the acne, the seborrheic dermatitis, the blemish, the effects of ageing, and the like subside. The composition is preferably administered one to eight times a day for from one day to a week or more until healing occurs.

Dosage forms of topical compositions, as described herein, include, for example, patches, ointments, creams, emulsions, liquids, lotions, gels, bioadhesive gels, aerosols, shampoos, pastes, foams, sunscreens, capsules, microcapsules, or in the form of an article or carrier, such as a bandage, insert, syringe-like applicator, pessary, powder, talc or other solid, shampoo, cleanser (leave on and wash off product), and agents that favor penetration within the epidermis, the dermis and keratin layers. Preferably, the topical composition, as described herein, is a liquid that can be easily applied to the area of pain.

The topical compositions, as described herein, can be applied to any bodily region needing treatment, including, for example, facial skin and other bodily skin.

The invention should now be illustrated with the following non-limiting examples. All ingredients were commercially available from a variety of sources. Unless otherwise indicated, all parts and percentages are by weight and all molecular weights are weight average molecular weight.

EXAMPLES

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

TABLE 1

| | Formulation | | | | | |
|---|---|---|---|---|---|---|
| Ingredient | Example 1 (for Oily Skin) | Weight % | Example 2 (for Dry Skin) | Weight % | Example 3 (for Normal Skin) | Weight % |
| Vinegar | 68 grams | 21.06 | 68 grams | 16.31 | 68 grams | 19.96 |
| Distilled Water | 168 grams | 52.01 | 224 grams | 53.75 | 168 grams | 49.31 |
| Xanthan gum | 9 grams | 2.78 | 9 grams | 2.15 | 9 grams | 2.64 |
| Salt | 46 grams | 14.2 | 40 grams | 9.59 | 38 grams | 11.15 |

TABLE 1-continued

| Ingredient | Example 1 (for Oily Skin) | | Weight % | Example 2 (for Dry Skin) | | Weight % | Example 3 (for Normal Skin) | | Weight % |
|---|---|---|---|---|---|---|---|---|---|
| Hibiscus Extract | 11 | grams | 3.4 | | | | | | |
| Essential Oil (Spearmint) | 0.112 | grams | 0.003 | | | | | | |
| Brown Sugar | 17 | grams | 5.26 | | | | | | |
| Ground Nutmeg | 1.0 | grams | 0.31 | | | | | | |
| Tea Leaves | 2 | grams | 0.62 | 1.5 | grams | 0.36 | | | |
| Essential Oil (Orange) | 0.75 | grams | 0.23 | 0.375 | grams | 0.08 | 1.31 | grams | 0.38 |
| Essential Oil (Eucalyptus) | | | | 0.75 | grams | 1.79 | | | |
| Elderberry Extract | | | | 27.2 | grams | 6.52 | | | |
| Sea Kelp | | | | 5 | grams | 1.19 | | | |
| Allspice | | | | 3 | grams | 0.72 | | | |
| Grape seed Oil | | | | 38 | grams | 9.11 | 12.7 | grams | 3.73 |
| Essential Oil (Rosemary) | | | | | | | 0.19 | grams | 0.06 |
| Lime Juice | | | | | | | 14 | grams | 4.10 |
| Ground Cloves | | | | | | | 1.5 | grams | 0.44 |
| Mint Extract | | | | | | | 27.2 | grams | 7.98 |
| Peppercorn | | | | | | | 0.75 | grams | 0.22 |
| Total | 322.86 | grams | 100.00 | 416.82 | grams | 100.00 | 340.65 | grams | 100.00 |

Example 1

Preparation of a Topical Composition for Oily Skin

To an open vessel was added about 168 grams of water (see Example 1 in Table 1) and heated to boiling with stirring. About 46 grams of sodium chloride was added and stirred to effect complete solution. To the sodium chloride solution was added about 68 grams of vinegar, about 2 grams of tea leaves, and about 9 grams of xanthan gum and stirred vigorously to afford a slurry.

To this slurry was added 11 grams of *Hibiscus* Extract, 0.112 grams of Essential Oil (Spearmint), 17 grams of Brown Sugar, 1.0 grams of Ground Nutmeg, and 0.75 grams of Essential Oil (Orange). The mixture was stirred vigorously, and cooled to room temperature.

Example 2

Preparation of a Topical Composition for Dry Skin

To an open vessel was added about 168 grams of water (see Example 2 in Table 1) and heated to boiling with stirring. A solution of about 40 grams of sodium chloride in 56 grams of water was added and stirred to effect complete solution. To the sodium chloride solution was added about 68 grams of vinegar, about 27.2 grams of elderberry extract, and about 38 grams of grape seed oil and stirred vigorously. To this mixture was added about 9 grams of xanthan gum and stiffed vigorously to afford a slurry.

To this slurry was added 3 grams of Allspice, 5 grams of Sea Kelp, 0.75 grams of Essential Oil (*Eucalyptus*), 0.375 grams of Essential Oil (Orange), and 1.5 grams of Tea Leaves. The mixture was stirred vigorously, and cooled to room temperature.

Example 3

Preparation of a Topical Composition for Normal Skin

To an open vessel was added about 168 grams of water (see Example 3 in Table 1) and heated to boiling with stirring. About 38 grams of sodium chloride was added and stirred to effect complete solution. To the sodium chloride solution was added about 68 grams of vinegar, and about 12.7 grams of grape seed oil and stirred vigorously. To this mixture was added about 9 grams of xanthan gum and stiffed vigorously to afford a slurry.

To this slurry was added 0.75 grams of Peppercorn, 27.2 grams of Mint Extract, 1.5 grams of Ground Cloves, 14 grams of Lime Juice, 0.19 grams of Essential Oil (Rosemary), and 12.7 grams of Grape seed Oil. The mixture was stirred vigorously, and cooled to room temperature.

Example 4

Application of the Topical Compositions

The topical compositions prepared in Examples 1-3 are applied to skin with a patient's finger or a soft cloth, allowed to remain in contact with the skin from about 30 seconds, to about 60 seconds, and rinsed off with water.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E"

shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

What is claimed is:

1. A topical composition consisting essentially of:
   about 21.1 weight percent vinegar;
   about 14.2 weight percent sodium chloride;
   about 2.8 weight percent xanthan gum;
   about 52.0 weight percent water;
   about 3.4 weight percent *hibiscus* extract;
   about 0.6 weight percent tea leaves;
   about 0.003 weight percent essential spearmint oil;
   about 0.2 weight percent essential orange oil;
   about 0.3 weight percent ground nutmeg; and
   about 5.26 weight percent brown sugar,
or
   about 16.3 weight percent vinegar;
   about 9.6 weight percent sodium chloride;
   about 2.1 weight percent xanthan gum;
   about 53.7 weight percent water;
   about 6.5 weight percent elderberry extract;
   about 9.1 weight percent grape seed oil;
   about 0.7 weight percent allspice;
   about 0.4 weight percent tea leaves;
   about 1.2 weight percent ground dried sea kelp;
   about 0.08 weight percent essential orange oil; and
   about 1.8 weight percent *eucalyptus* essential oil,
or
   about 19.9 weight percent vinegar;
   about 11.1 weight percent sodium chloride;
   about 2.6 weight percent xanthan gum;
   about 49.3 weight percent water;
   about 3.7 weight percent grape seed oil;
   about 4.1 weight percent lime juice;
   about 0.4 weight percent cloves;
   about 0.2 weight percent peppercorn;
   about 8.0 weight percent mint extract;
   about 0.4 weight percent orange essential orange oil; and
   about 0.1 weight percent essential rosemary oil.

2. The topical composition of claim 1, wherein the topical composition consists essentially of:
   about 21.1 weight percent vinegar;
   about 14.2 weight percent sodium chloride;
   about 2.8 weight percent xanthan gum;
   about 52.0 weight percent water;
   about 3.4 weight percent *hibiscus* extract;
   about 0.6 weight percent tea leaves;
   about 0.003 weight percent essential spearmint oil;
   about 0.2 weight percent essential orange oil;
   about 0.3 weight percent ground nutmeg; and
   about 5.26 weight percent brown sugar.

3. The topical composition of claim 1, wherein the topical composition consists essentially of:
   about 16.3 weight percent vinegar;
   about 9.6 weight percent sodium chloride;
   about 2.1 weight percent xanthan gum;
   about 53.7 weight percent water;
   about 6.5 weight percent elderberry extract;
   about 9.1 weight percent grape seed oil;
   about 0.7 weight percent allspice;
   about 0.4 weight percent tea leaves;
   about 1.2 weight percent ground dried sea kelp;
   about 0.08 weight percent essential orange oil; and
   about 1.8 weight percent *eucalyptus* essential oil.

4. The topical composition of claim 1, wherein the topical composition consists essentially of:
   about 19.9 weight percent vinegar;
   about 11.1 weight percent sodium chloride;
   about 2.6 weight percent xanthan gum;
   about 49.3 weight percent water;
   about 3.7 weight percent grape seed oil;
   about 4.1 weight percent lime juice;
   about 0.4 weight percent cloves;
   about 0.2 weight percent peppercorn;
   about 8.0 weight percent mint extract;
   about 0.4 weight percent orange essential orange oil; and
   about 0.1 weight percent essential rosemary oil.

* * * * *